United States Patent
Yamashita et al.

(10) Patent No.: US 9,355,445 B2
(45) Date of Patent: May 31, 2016

(54) BREAST CANCER PATHOLOGICAL IMAGE DIAGNOSIS SUPPORT SYSTEM, BREAST CANCER PATHOLOGICAL IMAGE DIAGNOSIS SUPPORT METHOD, AND RECORDING MEDIUM RECORDING BREAST CANCER PATHOLOGICAL IMAGE DIAGNOSIS SUPPORT PROGRAM

(75) Inventors: Yoshiko Yamashita, Tokyo (JP); Kenji Okajima, Tokyo (JP); Akira Sato, Tokyo (JP)

(73) Assignee: NEC CORPORATION, Tokyo (JP)

( * ) Notice: Subject to any disclaimer, the term of this patent is extended or adjusted under 35 U.S.C. 154(b) by 1274 days.

(21) Appl. No.: 12/529,402

(22) PCT Filed: Feb. 20, 2008

(86) PCT No.: PCT/JP2008/000277
§ 371 (c)(1),
(2), (4) Date: Oct. 8, 2009

(87) PCT Pub. No.: WO2008/108059
PCT Pub. Date: Sep. 12, 2008

(65) Prior Publication Data
US 2010/0054560 A1    Mar. 4, 2010

(30) Foreign Application Priority Data
Mar. 1, 2007 (JP) ................... 2007-051715

(51) Int. Cl.
*G06K 9/00* (2006.01)
*G06T 7/00* (2006.01)
(Continued)

(52) U.S. Cl.
CPC ............... *G06T 7/0012* (2013.01); *A61B 5/055* (2013.01); *G01N 1/30* (2013.01); *G01N 33/57415* (2013.01)

(58) Field of Classification Search
USPC ........................................................ 382/128
See application file for complete search history.

(56) References Cited

U.S. PATENT DOCUMENTS 6,546,123 B1    4/2003    McLaren et al.
2001/0044124 A1    11/2001    Bacus
(Continued)

FOREIGN PATENT DOCUMENTS

JP    1-123153 A    5/1989
JP    05-159056 A    6/1993
(Continued)

OTHER PUBLICATIONS

Lester J. Layfield, et al., "Assessment of Tissue Estrogen and Progesterone Receptor Levels: A Survey of Current Practice, Techniques, and Quantitation Method", The Breast Journal, May 2000, pp. 189-196, vol. 6, No. 3, Blackwell Publishing.
(Continued)

*Primary Examiner* — Victoria P Shumate
*Assistant Examiner* — Reginald R Reyes
(74) *Attorney, Agent, or Firm* — Sughrue Mion, PLLC

(57) ABSTRACT

A breast cancer pathological image diagnosis support system for supporting a diagnosis of breast cancer based on a pathological image is provided. The breast cancer pathological image diagnosis support system includes an image obtaining unit which obtains an HE-stained image and an IHC image as pathological images to be diagnosed; an information obtaining unit which obtains information of a tumor area in the HE-stained image; a matching unit which calculates a matching position of the HE-stained image and the IHC image obtained by the image obtaining unit; a specifying unit which specifies a tumor area in the IHC image based on the information of the tumor area in the HE-stained image obtained by the information obtaining unit and information of the matching position calculated by the matching unit; and a calculating unit which calculates a staining positive cell content rate in the tumor area based on information of the tumor area in the IHC image specified by the specifying unit.

28 Claims, 12 Drawing Sheets

(51) Int. Cl.
*A61B 5/055* (2006.01)
*G01N 1/30* (2006.01)
*G01N 33/574* (2006.01)

(56) References Cited

U.S. PATENT DOCUMENTS

| | | | |
|---|---|---|---|
| 2002/0177149 A1 | 11/2002 | Rimm et al. | |
| 2003/0059851 A1* | 3/2003 | Smith | G01N 1/30 435/7.2 |
| 2006/0247514 A1* | 11/2006 | Panasyuk | A61B 5/0059 600/410 |
| 2007/0135999 A1* | 6/2007 | Kolatt | G01N 21/31 702/19 |
| 2007/0172100 A1 | 7/2007 | Lefebvre | |
| 2007/0176103 A1* | 8/2007 | Inada | G01N 23/04 250/311 |
| 2010/0080757 A1* | 4/2010 | Haaga | A61B 5/0263 424/9.3 |

FOREIGN PATENT DOCUMENTS

| | | |
|---|---|---|
| JP | 06-094706 A | 4/1994 |
| JP | 2002-282215 A | 10/2002 |
| JP | 2003-504627 A | 2/2003 |
| JP | 2003-519796 A | 6/2003 |
| JP | 2004-532410 A | 10/2004 |
| JP | 2006-153742 A | 6/2006 |
| JP | 2006-308338 A | 11/2006 |
| JP | 2007-192821 A | 8/2007 |

OTHER PUBLICATIONS

Yoichi Tani, "Image analysis of immunostained pathological specimens for molecular-target targeted therapy", The Cell, Aug. 20, 2002, pp. 32 to 35, vol. 34, No. 9.

Communication, dated May 14, 2013, issued by the Japanese Patent Office in counterpart Japanese Patent Application No. 2009-502443.

* cited by examiner

FIG. 2

| SUBJECT IDENTIFIER /201 | IMAGE IDENTIFIER 1 /202 | IMAGE IDENTIFIER 2 /202 | ... /202 | IMAGE IDENTIFIER n /202 | SPECIMEN ADJACENT INFORMATION /205 |
|---|---|---|---|---|---|
| | STAINING INFORMATION 1 /203 | STAINING INFORMATION 2 /203 | ... /203 | STAINING INFORMATION n /203 | |
| | IMAGE DATA 1 /204 | IMAGE DATA 2 /204 | ... /204 | IMAGE DATA n /204 | |
| | TUMOR AREA INFORMATION 1 /206 | TUMOR AREA INFORMATION 2 /206 | ... /206 | TUMOR AREA INFORMATION n /206 | |

BREAST CANCER PATHOLOGICAL IMAGE DIAGNOSIS SUPPORT SYSTEM, BREAST CANCER PATHOLOGICAL IMAGE DIAGNOSIS SUPPORT METHOD, AND RECORDING MEDIUM RECORDING BREAST CANCER PATHOLOGICAL IMAGE DIAGNOSIS SUPPORT PROGRAM

CROSS REFERENCE TO RELATED APPLICATION

This application is a National Stage of International Application No. PCT/JP2008/000277 filed Feb. 20, 2008, claiming priority based on Japanese Patent Application No. 2007-051715, filed Mar. 1, 2007, the contents of all of which are incorporated herein by reference in their entirety.

TECHNICAL FIELD

The present invention relates to a system, a method, a program and a recording medium for supporting a diagnosis of breast cancer based on a pathological image.

BACKGROUND ART

A pathological diagnosis is performed by viewing a microscope glass specimen referred to as a preparation with a microscope. The microscope specimen, which is made of an organ, tissue and a cell collected from a patient, is obtained by thinly slicing a sample into a few micron thick and thereafter staining the same. A microscopic observation of the specimen supports the diagnosis of illness by a doctor, and is used to determine a future approach to treatment and a prognosis. Especially, an observation of immunohistochemical staining (IHC, also simply referred to as immunostaining) in the breast cancer is used to determine a future indication for endocrine therapy.

An effect indicator of the endocrine therapy in the breast cancer is determined by occupancy or the like of estrogen receptor (ER) or progesterone receptor (PgR) positive cells of which cell nucleus is stained in tumor cells in the tissue. A tumor diagnosis is performed by the microscopic observation of a hematoxylin-eosin stained (HE-stained) specimen of a tissue section. Also, the indication determination for the endocrine therapy is diagnosed by the microscopic observation of the tissue section specimen stained by the immunohistochemical staining.

Therefore, the indication determination for the endocrine therapy in the breast cancer is diagnosed according to a following procedure. First, a pathologist determines the tumor by the microscopic observation of the HE-stained tissue section specimen by using an HE-stained tissue section and an immunohistochemically-stained tissue section adjacent to each other. Subsequently, the tissue section specimen obtained by staining the tissue section adjacent to the HE-stained tissue section by the immunohistochemical staining is checked against a portion corresponding to the tumor portion determined by the HE-staining. Thereby, a tumor portion is distinguished in the immunohistochemically-stained tissue section specimen. Then, the distinguished tumor portion of the immunohistochemically-stained tissue section specimen is microscopically observed.

Although this pathological test is one of a test methods generally performed in current medical institutions, standardization of an examination method and an evaluation method of the immunohistochemical staining is not realized. Although an automatic staining device for staining the tissue section is widely used and the number of cases of the pathological tests increases in these years, the number of pathologists is overwhelmingly small.

The HE-staining is the most general staining in which the cell nucleus is stained in blue by hematoxylin and a cell cytoplasm and connective tissue are stained in pink by eosin. The tumor is diagnosed by the observation of the HE-staining. At that time, the tumor is determined by direct microscopic observation of a pathological slide by the pathologist. On the other hand, it is also performed that the pathological slide is imaged and converted into an electric image, the pathological image is displayed on a computer display, and the image is observed by the pathologist and determined. Also, an example of the support system for the tumor diagnosis is disclosed in the Patent Document 1 (Japanese Patent Publication (Tokkai) No. 2006-153742).

The immunohistochemical staining is a method of detecting a local existence of target protein in the cell and in the tissue by utilizing specific binding reaction, which is antigen antibody reaction. That is to say, this is a method of determining whether the tumor cell itself produces a tumor marker, and this stains a substance referred to as the tumor marker. In the immunohistochemical staining, a chromogenic substrate referred to as diaminobenzidine (DAB), which stains in brownish red, is used, and a method of producing a color by DAB and staining the nucleus by hematoxylin is widely used. Principal tests by the immunohistochemical staining include an ER test, a PgR test and a HER-2 test. In the ER test and the PgR test, expression of ER and PgR is evaluated by the immunohistochemical staining, and when ER and PgR are positive, almost all of the tumor cell nuclei are stained in brown.

There are some determining criteria of the ER test and the PgR test by the immunohistochemical staining, such as a criterion based on only a staining positive cell content rate and a criterion based on a combination of the staining positive cell content rate and staining intensity, and there are various cut off values (Non-Patent Document 1: Leyfield L J, Guputa D, Mooney E E, "Assessment of tissue estrogen and progesterone receptor levels: a survey of current practice, techniques, and quantitation method", Blackwell Publishing, The Breast Journal, Volume 6, Number 3, May 2000, pp. 189-196 (8).)

Meanwhile, as the related art documents relating to the present invention, there are the Patent Document 2 (Japanese Patent Publication (Tokkai) No. 2002-282215), the Patent Document 3 (Japanese Patent Publication (Tokkaihei) No. 05-159056), the Patent Document 4 (Japanese Patent Publication (Tokkaihei) No. 06-94706), and the Patent Document 5 (Japanese Patent Publication (Tokuhyo) No. 2004-532410) in addition to the Patent Document 1 and the Non-patent Literature 1.

[Patent Document 1] Japanese Patent Publication (Tokkai) No. 2006-153742
[Patent Document 2] Japanese Patent Publication (Tokkai) No. 2002-282215
[Patent Document 3] Japanese Patent Publication (Tokkaihei) No. 05-159056
[Patent Document 4] Japanese Patent Publication (Tokkaihei) No. 06-94706
[Patent Document 5] Japanese Patent Publication (Tokuhyo) No. 2004-532410
[Non-patent Literature 1] Leyfield L J, Guputa D, Mooney E E, "Assessment of tissue estrogen and progesterone receptor levels: a survey of current practice, techniques, and quantitation method", Blackwell Publishing, The Breast Journal, Volume 6, Number 3, May 2000, pp. 189-196 (8).

DISCLOSURE OF THE INVENTION

Problem to be Solved by the Invention

However, since the evaluation of the conventional ER test, PgR test and the like is performed based on a result obtained by counting the number of expressions of the staining positive cells by visual contact in the microscopic observation by the pathologist, this has been semi-quantitative. In this regard, since the count of the number of expressions is performed by the visual contact by the pathologist even when a system in which image information obtained by imaging the slide is displayed on the display is used, the evaluation has been semi-quantitative.

Means for Solving Problem

According to the present invention, there is provided a breast cancer pathological image diagnosis support system for supporting a diagnosis of breast cancer based on a pathological image, including an image obtaining unit which obtains an HE-stained image and an IHC image as pathological images to be diagnosed, an information obtaining unit which obtains information of a tumor area in the HE-stained image, a matching unit which calculates a matching position of the HE-stained image and the IHC image obtained by the image obtaining unit, a specifying unit which specifies a tumor area in the IHC image based on the information of the tumor area in the HE-stained image obtained by the information obtaining unit and information of the matching position calculated by the matching unit, and a calculating unit which calculates a staining positive cell content rate in the tumor area based on information of the tumor area in the IHC image specified by the specifying unit.

In the system, the HE-stained image and the IHC image are obtained by the image obtaining unit, and the information of the tumor area in the HE-stained image is obtained by the information obtaining unit. Thereafter, the matching position of the HE-stained image and the IHC image is calculated by the matching unit. Subsequently, the tumor area in the IHC image is specified by the specifying unit based on the information of the tumor area in the HE-stained image and the information of the matching position. Then, the staining positive cell content rate in the tumor area in the IHC image is calculated by the calculating unit based on the information of the tumor area in the IHC image. Thereby, the staining positive cell content rate can be obtained as a quantitative value.

According to the present invention, there is provided a breast cancer pathological image diagnosis support method of supporting a diagnosis of breast cancer based on a pathological image, including obtaining an HE-stained image and an IHC image as pathological images to be diagnosed, obtaining information of a tumor area in the HE-stained image, matching images to calculate a matching position of the HE-stained image and the IHC image obtained at the obtaining images, specifying a tumor area in the IHC image based on the information of the tumor area in the HE-stained image obtained at the obtaining information and information of the matching position calculated at the matching, and calculating a staining positive cell content rate in the tumor area based on information of the tumor area in the IHC image specified at the specifying.

According to the present invention, there is provided a breast cancer pathological image diagnosis support program for supporting a diagnosis of breast cancer based on a pathological image, causing a computer to execute an image obtaining procedure of obtaining an HE-stained image and an IHC image as pathological images to be diagnosed, an information obtaining procedure of obtaining information of a tumor area in the HE-stained image, a matching procedure of calculating a matching position of the HE-stained image and the IHC image obtained at the image obtaining procedure, a specifying procedure of specifying a tumor area in the IHC image based on the information of the tumor area in the HE-stained image obtained at the information obtaining procedure and information of the matching position calculated at the matching procedure, and a calculating procedure of calculating a staining positive cell content rate in the tumor area based on information of the tumor area in the IHC image specified at the specifying procedure.

According to the present invention, there is provided a recording medium recording a program for supporting a diagnosis of breast cancer based on a pathological image, being a computer readable recording medium recording a program for causing a computer to execute an image obtaining procedure of obtaining an HE-stained image and an IHC image as pathological images to be diagnosed, an information obtaining procedure of obtaining information of a tumor area in the HE-stained image, a matching procedure of calculating a matching position of the HE-stained image and the IHC image obtained at the image obtaining procedure, a specifying procedure of specifying a tumor area in the IHC image based on the information of the tumor area in the HE-stained image obtained at the information obtaining procedure and information of the matching position calculated at the matching procedure, and a calculating procedure of calculating a staining positive cell content rate in the tumor area based on information of the tumor area in the IHC image specified at the specifying procedure.

According to the method, the program and the recording medium, the HE-stained image and the IHC image are obtained at the image obtaining procedure, and the information of the tumor area in the HE-stained image is obtained at the information obtaining procedure. Thereafter, the matching position of the HE-stained image and the IHC image is calculated at the matching procedure. Subsequently, the tumor area in the IHC image is specified at the specifying procedure based on the information of the tumor area in the HE-stained image and the information of the matching position. Then, the staining positive cell content rate in the tumor area in the IHC image is calculated at the calculating procedure based on the information of the tumor area in the IHC image. Thereby, the staining positive cell content rate may be obtained as the quantitative value.

According to the present invention, the breast cancer pathological image diagnosis support system, the breast cancer pathological image diagnosis support method, the breast cancer pathological image diagnosis support program and the recording medium, capable of obtaining the staining positive cell content rate as the quantitative value, may be realized.

BRIEF DESCRIPTION OF THE DRAWINGS

FIG. 2 is a view for illustrating content of a staining image database.

BEST MODE FOR CARRYING OUT THE INVENTION

Figure 1:
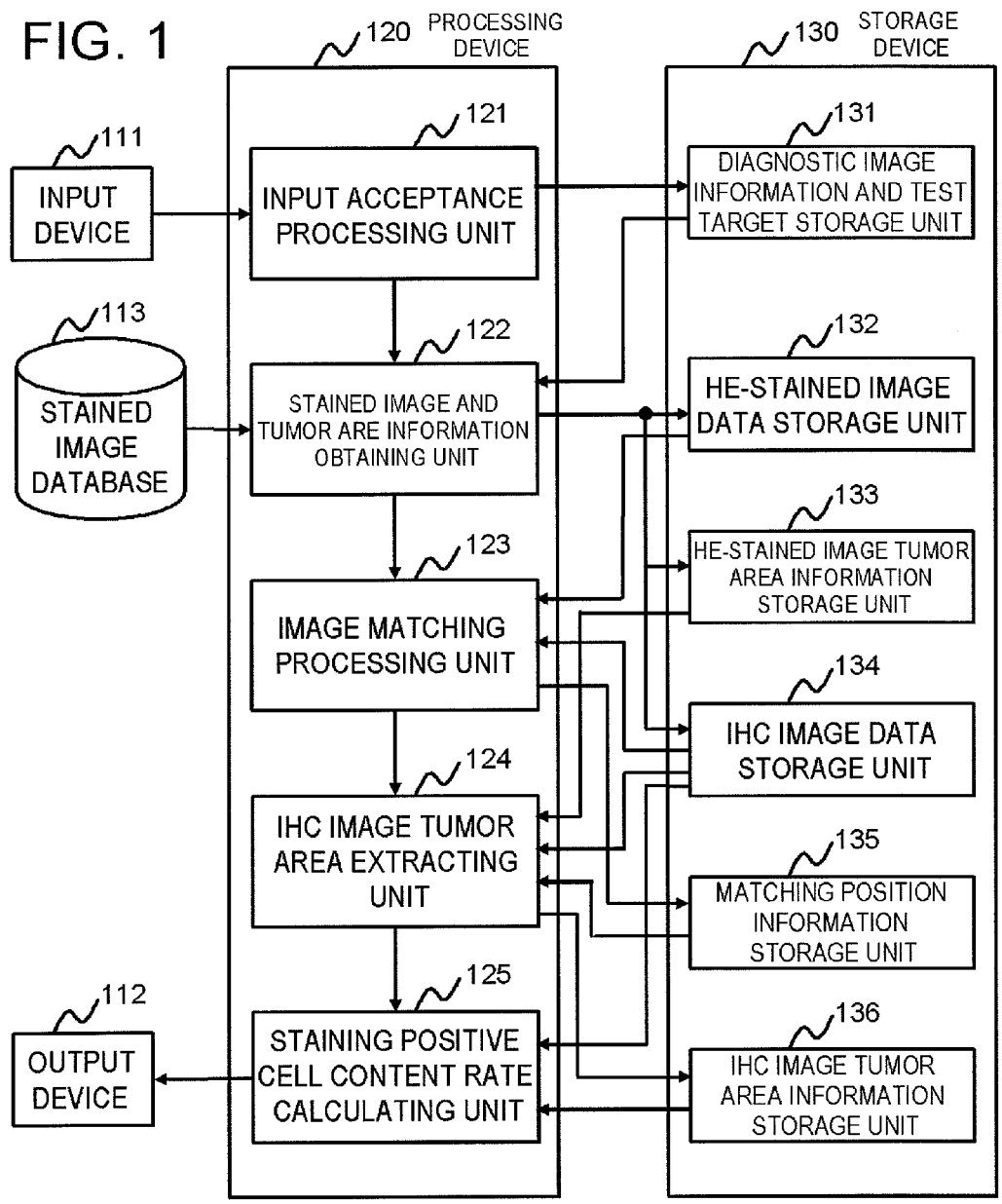
FIG. 1 is a block diagram showing a first exemplary embodiment of a breast cancer pathological image diagnosis support system according to the present invention.

Hereinafter, an exemplary embodiment of the present invention is described in detail with reference to drawings. Meanwhile, in the description of the drawings, the same reference numeral is given to the same component and an overlapped description thereof will not be repeated.

First Exemplary Embodiment

FIG. 1 is a block diagram showing a first exemplary embodiment of a breast cancer pathological image diagnosis support system according to the present invention. This system is a system for supporting a diagnosis of breast cancer based on a pathological image, and includes an image obtaining unit which obtains an HE-stained image and an IHC image as the pathological images to be diagnosed, an information obtaining unit which obtains information of a tumor area in the HE-stained image, a matching unit which calculates a matching position of the HE-stained image and the IHC image obtained by the image obtaining unit, a specifying unit which specifies a tumor area in the IHC image based on the information of the tumor area in the HE-stained image obtained by the information obtaining unit and information of the matching position calculated by the matching unit, and a calculating unit which calculates a staining positive cell content rate in the tumor area based on information of the tumor area in the IHC image specified by the specifying unit.

In more detail, the system of this exemplary embodiment includes an input device 111, an output device 112, a stained image database 113, a processing device 120, and a storage device 130.

The stained image database 113 stores one or more HE-stained image, the IHC image, which is a specimen of a serial section adjacent to a specimen of the HE-stained image, specimen adjacent information of the above-described HE-stained image and the above-described IHC image, and tumor area information calculated from the above-described HE-stained image or determined by a doctor or the like.

Each image has a subject identifier by which relevant information regarding a subject is related with each image. For example, as shown in FIG. 2, a subject identifier 201 for uniquely identifying the subject, an image identifier 202, staining information 203, image data 204, specimen adjacent information 205, HE-stained image tumor area information 206 are included.

The image identifier 202 is an identifier for identifying a plurality of pathological images for the subject. The staining information 203, the image data 204 and the tumor area information 206 are distinguished from those of other images by the image identifier 202. Each staining information 203 indicates the staining information of the image, and HE, ER and PgR are stored, for example. Each image data 204 stores an image data. The specimen adjacent information 205 stores correspondence relationship by using the image identifier 202. The HE-stained image tumor area information 206 stores the tumor area information calculated from the HE-stained image or determined by the doctor or the like. Meanwhile, the HE-stained image tumor area information 206 may be made correspond to the image identifier 202 and separately stored.

Normal input/output devices provided on a computer may be used as the input device 111 and the output device 112. For example, the input device 111 is a keyboard and a mouse, and the output device 112 is a display device and a printer. Meanwhile, the input device 111 and the output device 112 may be an input file and an output file, or may be another computer or the like.

The storage device 130 is composed of a main storage device and an auxiliary storage device provided on the computer, and is used for holding various programs executed in the processing device 120 and data. The processing device 120 includes a CPU of the computer and operates by program control.

The processing device 120 includes an input acceptance processing unit 121, a stained image and tumor area information obtaining unit 122, an image matching processing unit 123 (matching unit), an IHC image tumor area extracting unit 124 (specifying unit), and a staining positive cell content rate calculating unit 125 (calculating unit). The stained image and tumor area information obtaining unit 122 combines functions of the above-described image obtaining unit and information obtaining unit.

The input acceptance processing unit 121 accepts specification information of the pathological image to be diagnosed and specification information of a test type (ER test or PgR test) from a user or the like by means of the input device 111. Further, the input acceptance processing unit 121 stores the pieces of information in a diagnostic image information and test target storage unit 131 of the storage device 130, and shifts the process to the stained image and tumor area information obtaining unit 122. In a case of this exemplary embodiment, the specification information of the pathological image is the image identifier. The image identifier is the HE-stained image or the IHC image, and it is possible to specify one or a plurality of them. Also, the specification information of the test type is an IHC test item, and it is possible to specify one or both of the ER test and the PgR test.

The stained image and tumor area information obtaining unit 122 obtains the HE-stained image and the IHC image to be diagnosed and the information of the tumor area in the HE-stained image from the stained image database 113, to store them, respectively, in an HE-stained image data storage unit 132, an IHC image data storage unit 134 and an HE-stained image tumor area information storage unit 133 in the storage device 130, and shifts the process to the image matching processing unit 123.

In a case in which the staining information 203 having the image identifier stored in the diagnostic image information and test target storage unit 131 is HE staining, the image data 204 having the corresponding image identifier is stored in the HE-stained image data storage unit 132. Also, by referring to the test type stored in the diagnostic image information and test target storage unit 131 and the specimen adjacent information 205, the image data 204 of the IHC image, which is the serial section specimen adjacent to the HE image specimen to be diagnosed, is stored in the IHC image data storage unit 134. Further, the information of the HE-stained image tumor area information 206 is stored in the HE-stained image tumor area information storage unit 133.

On the other hand, in a case in which the staining information 203 having the image identifier stored in the diagnostic image information and test target storage unit 131 is IHC, the image data 204 having the corresponding image identifier is stored in the IHC image data storage unit 134. Also, by referring to the specimen adjacent information 205, the image data 204 of the HE-stained image, which is the serial section specimen adjacent to the IHC image specimen to be diagnosed, is stored in the HE-stained image data storage unit 132. Further, the information of the HE-stained image tumor area information 206 is stored in the HE-stained image tumor area information storage unit 133. When a plurality of image identifiers are specified, it is searched for each of them to associate to store.

The image matching processing unit 123 reads the HE-stained image and the IHC image from the HE-stained image data storage unit 132 and the IHC image data storage unit 134, respectively, and calculates the matching position of the HE-stored image and the IHC image. Further, the image matching processing unit 123 stores the matching position information (rotational angle and horizontal/vertical misalignment width) in a matching position information storage unit 135, and shifts the process to the IHC image tumor area extracting unit 124. Since the HE-stained image and the IHC image are the serial sections, they may be very similar to each other. However, due to difference in staining, the colors thereof are completely different, that is, the HE-stained image is in blue and pink and the IHC image is in brownish read and blue. In the image matching, each image is binalized, and phase-only correlation method, sequential similarity detection algorithm and a method of using a unique point may be used.

The IHC image tumor area extracting unit 124 reads the HE-stained image tumor area information, the IHC image data and the matching position information from the HE-stained image tumor area information storage unit 133, the IHC image data storage unit 134 and the matching position information storage unit 135, respectively, and calculates the tumor area in the IHC image data. Further, the IHC image tumor area extracting unit 124 stores the information of the tumor area in the IHC image data in the IHC image tumor area information storage unit 136, and shifts the process to the staining positive cell content rate calculating unit 125.

The staining positive cell content rate calculating unit 125 reads the IHC image data and the tumor area information from the IHC image data storage unit 134 and the IHC image tumor area information storage unit 136, respectively, counts the number of staining positive cell nuclei and the number of staining negative cell nuclei in the tumor area, and calculates the staining positive cell content rate to output from the output device 112.

An example of operation of the system shown in FIG. 1 will be described below as the first exemplary embodiment of a breast cancer pathological image diagnosis support method and a breast cancer pathological image diagnosis support program according to the present invention with reference to flowcharts shown in FIGS. 3 to 6. In summary, this is the method of supporting the diagnosis of the breast cancer based on the pathological image and includes following steps (a) to (e). Also, the program of this exemplary embodiment is a program for supporting the diagnosis of the breast cancer based on the pathological image, which causes the computer to execute the steps (a) to (e).

(a) An image obtaining step of obtaining the HE-stained image and the IHC image as the pathological images to be diagnosed.

(b) An information obtaining step of obtaining the information of the tumor area in the HE-stained image.

(c) A matching step of calculating the matching position of the HE-stained image and the IHC image obtained at the image obtaining step.

(d) A specifying step of specifying the tumor area in the IHC image based on the information of the tumor area in the HE-stained image obtained at the information obtaining step and the information of the matching position calculated at the matching step.

(e) A calculating step of calculating the staining positive cell content rate in the tumor area based on the information of the tumor area in the IHC image specified at the specifying step.

Figure 3:
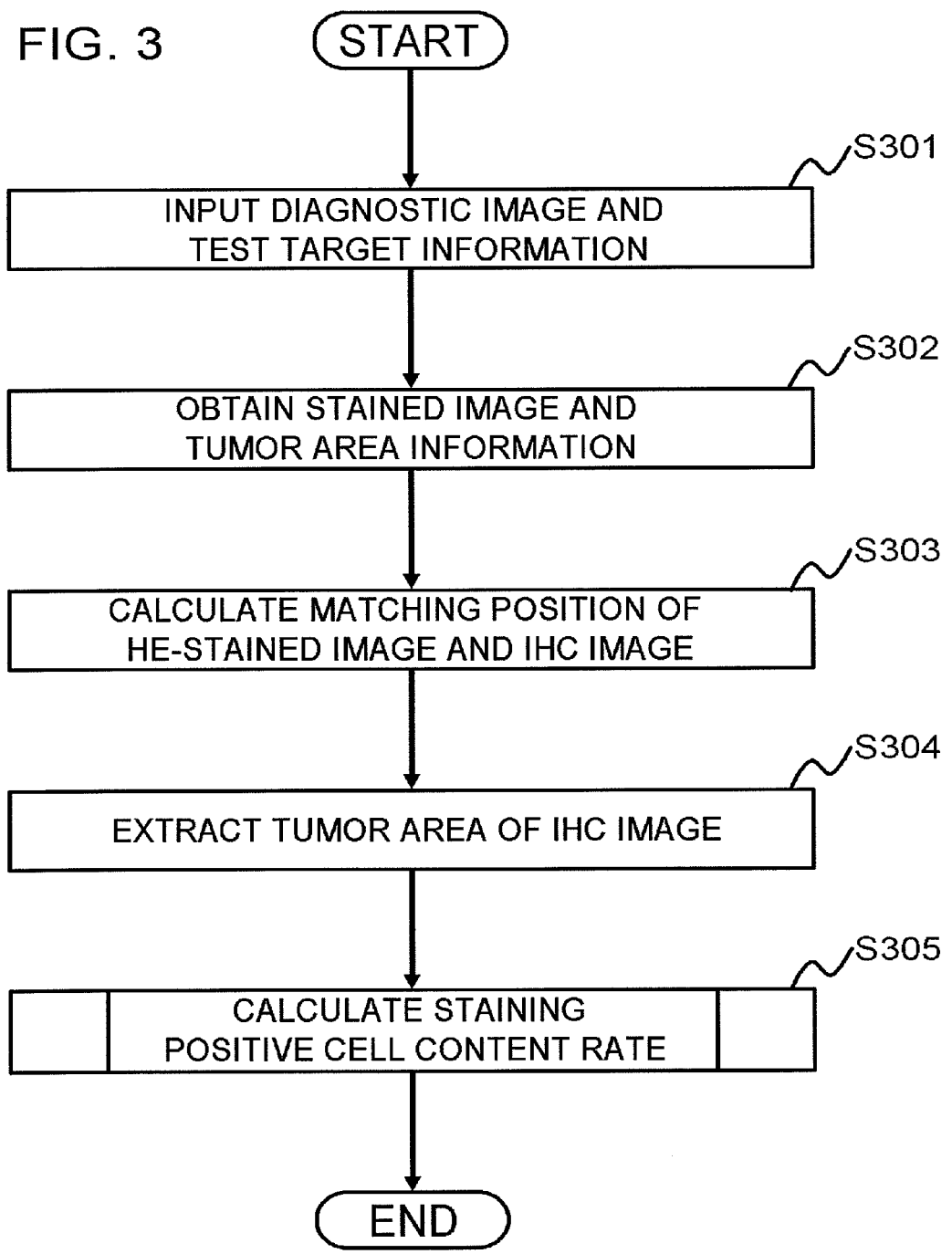
FIG. 3 is a flowchart for illustrating an example of operation of the system shown in FIG. 1.

In more detail, when starting the process, the subject identifier 201, the image identifier 202, the staining information 203, the image data 204, the specimen adjacent information 205, and the HE-stained image tumor area information 206, all of which are a series of data for the subject, are stored in the stained image database 113. The tumor area information 206 is the information obtained by calculating the tumor area from the HE-stained image in advance, or the tumor area information specified by the doctor. When the processing device 120 is activated in such a state, a process shown in FIG. 3 is started.

First, when the image identifier of the HE-stained image or the image identifier of the IHC image, which specifies the diagnostic image, and an IHC test item request, which specifies the test target, are supplied from the input device 111 to the input acceptance processing unit 121 of the processing device 120, the input acceptance processing unit 121 passes the diagnostic image specification information and the test target specification information to the stained image and tumor area information obtaining unit 122 through the diagnostic image information and test target storage unit 131 of the storage unit 130. Then, the process shifts to the stained image and tumor area information obtaining unit 122 (step S301).

Next, the stained image and tumor area information obtaining unit 122 searches the stained image database 113 for the image identifier in the diagnostic image information and test target storage unit 131, and when the staining information 203 having the specified image identifier is the HE staining, the stained image and tumor area information obtaining unit 122 stores the image data 204 having the image identifier in the HE-stained image data storage unit 132. Further, the HE-stained image tumor area information 206 is stored in the HE-stained image tumor area information storage unit 133. Also, the IHC test item in the diagnostic image information and test target storage unit 131 is read, the specimen adjacent information 205 in the stained image database 113 is referred to, and the IHC image data 204, which is the serial section specimen adjacent to the HE-stained image, is stored in the IHC image data storage unit 134.

On the other hand, when the staining information 203 having the specified image identifier is the IHC, the image data 204 having the image identifier is stored in the IHC image data storage unit 134. Also, the specimen adjacent information 205 of the stained image database 113 is referred to, and the HE-stained image data 204, which is the serial section specimen adjacent to the IHC image, is stored in the HE-stained image data storage unit 132. Further, the HE-stained image tumor area information 206 is stored in the HE-stained image tumor area information storage unit 133. Then, the process shifts to the image matching processing unit 123 (step S302).

The image matching processing unit 123 calculates the matching position of the HE-stained image and the IHC image by using the phase-only correlation method after adjusting a color scale of each image, for example, from the HE-stained image stored in the HE-stained image data storage unit 132 and the IHC image stored in the IHC image data storage unit 134, and stores the matching position information (rotational angle and horizontal/vertical misalignment width) in the matching position information storage unit 135. Then, the process shifts to the IHC image tumor area extracting unit 124 (step S303).

The IHC image tumor area extracting unit 124 calculates the tumor area in the IHC image stored in the IHC image data storage unit 134 from the tumor area information of the HE-stained image stored in the HE-stained image tumor area information storage unit 133 and the matching position information stored in the matching position information storage unit 135, and stores the tumor area information of the IHC image in the IHC image tumor area information storage unit 136. Then, the process shifts to the staining positive cell content rate calculating unit 125 (step S304).

The staining positive cell content rate calculating unit 125 receives the IHC image data stored in the IHC image data storage unit 134 and the tumor area stored in the IHC image tumor area information storage unit 136, counts the number of staining positive cell nuclei and the number of staining negative cell nuclei in the tumor area, and calculates the staining positive cell content rate to output from the output device 112 (step S305). Since the staining positive cell nucleus is stained in brownish read and the staining negative cell nucleus is stained in blue, the number of nuclei stained in brown and the number of nuclei stained in blue are counted. The process is performed according to procedures shown in FIGS. 4, 5 and 6.

First, an outside of the tumor area of the IHC image data is masked based on the received IHC image data and tumor area (step S401), and in the tumor area, a brown area, which is an area stained in brown, and a blue area, which is an area stained in blue, are identified by discrimination analysis (step S402).

In the process, first, the image data is converted into a HSV color space (step S501), an unstained area is removed according to S (saturation) and V (value) (step S502), and a value range of H (hue) is converted from [0, 1] to [0.3, 1.3] (step S503). Next, it is checked whether the H (hue) value of all the pixels are included in either of [0.3, 0.8) range and [0.8, 1.3) range (step S504), and when all the pixels are included in one area, [0.3, 0.8) is output as the blue area and [0.8, 1.3] is output as the brown area (step S507). When the pixels are present in both areas, a threshold t is calculated by the discrimination analysis (step S505), and [0.3, t) is output as the blue area and [t, 1.3) is output as the brown area (step S506).

Next, nuclear extraction is performed in the brown area (step S403), and subsequently the nuclear extraction is performed in the blue area (step S404). In these processes, first, when the brown area or the blue area is input (step S601), a V' value obtained by emphasizing the V value with a sigmoid function is calculated in consideration of average and dispersion of the V (value) value (step S602), and the V' value is converted into a binary image by setting the V' value with a certain threshold such that a value not larger than the threshold is within a nuclear area (=1) and a value larger than the threshold is outside of the nuclear area (=0) (step S603). Next, a position of the nucleus is calculated by performing adjacent pixel comparison by applying a Gaussian filter to the binary image (step S604).

Next, the number of nuclei detected in the brown area is counted (step S405), the number of nuclei detected in the blue area is counted (step S406), and finally, a ratio of the number of brown nuclei to a total number of nuclei, that is to say, the number of brown nuclei/(the number of brown nuclei+the number of blue nuclei) is calculated (step S407).

An effect of this exemplary embodiment will be described below. In this exemplary embodiment, the HE-stained image and the IHC image are obtained by the image obtaining unit, and the information of the tumor area in the HE-stained image is obtained by the information obtaining unit. Thereafter, the matching position of the HE-stained image and the IHC image is calculated by the matching unit. Subsequently, the tumor area in the IHC image is specified by the specifying unit based on the information of the tumor area in the HE-stained image and the information of the matching position. Then, the staining positive cell content rate in the tumor area in the IHC image is calculated by the calculating unit based on the information of the tumor area in the IHC image. Thereby, the staining positive cell content rate may be obtained as a quantitative value.

As a result, it becomes possible that the doctor may perform the diagnosis by immunohistochemical staining based on the quantitative value. This is helpful in determining a cut off value in the determination of the ER test and the PgR test. On the other hand, conventionally, an evaluation of the ER test and the PgR test has been semiquantitative, as described above. Therefore, since the evaluation of a test result varies in each measurement, this has been problematic in determining the cut off value.

Further, since the number of cases of tissue diagnosis and cytological diagnosis is increasing and the number of pathologists is relatively small, conventionally, there has been a problem that the pathologists are forced to work for a long time. In this regard, according to this exemplary embodiment, labor burden of the doctors or the like can be reduced.

In addition, according to this exemplary embodiment, the tumor area determined in the HE-stained image may be associated with the IHC image by the matching of the HE-stained image and the IHC image, which are the serial section specimen images. Also, by applying the discrimination analysis to the H (hue) value, the brown area and the blue area may be identified. Further, by performing the nuclear extraction in each of the brown area and the blue area, the ratio of the number of brown nuclei to the total number of nuclei may be calculated. Therefore, it is possible to provide information helpful to the diagnosis by the doctor, thereby supporting the diagnosis, by presenting the staining positive cell content rate to the doctors or the like.

Second Exemplary Embodiment

Figure 7:
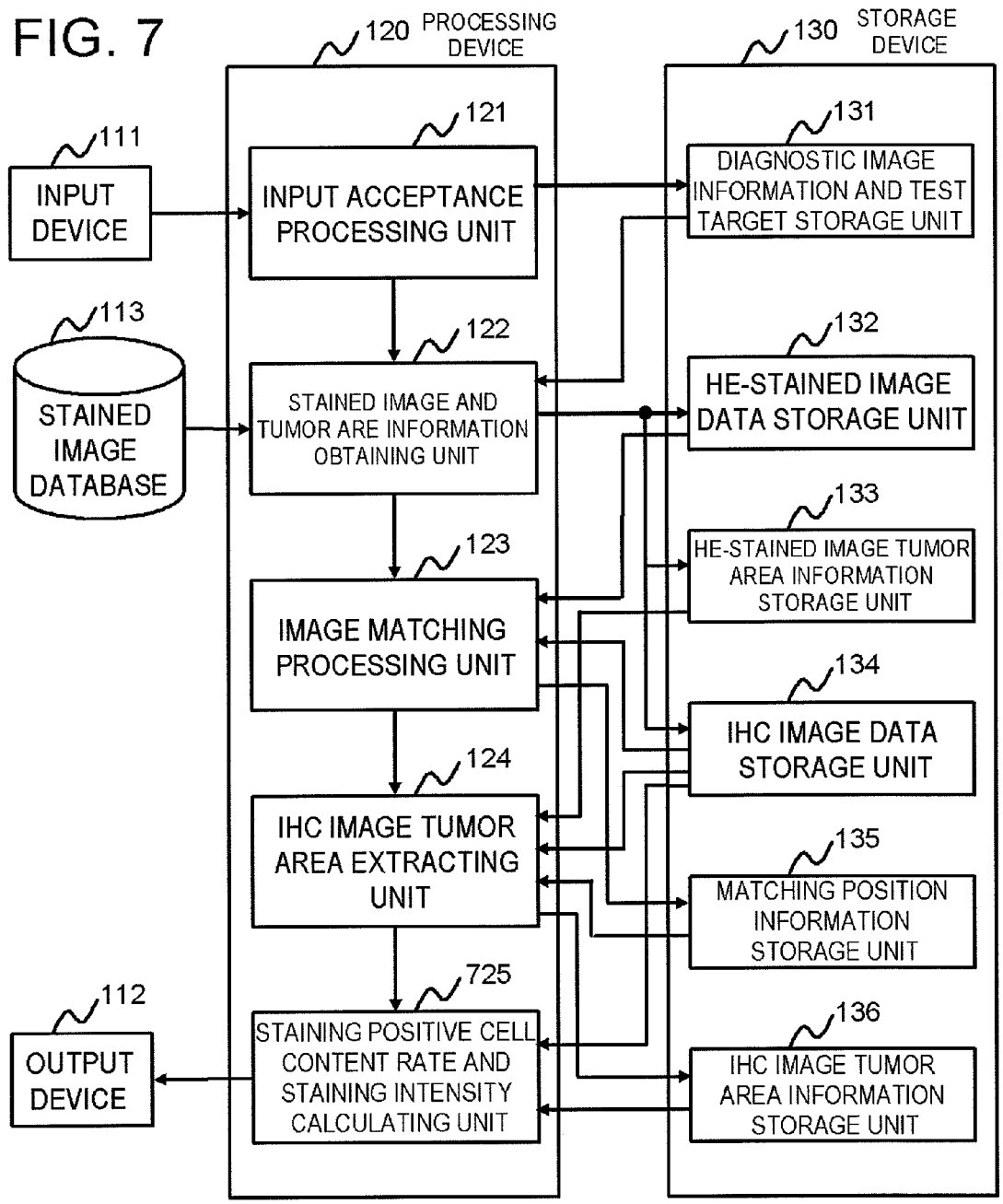
FIG. 7 is a block diagram showing a second exemplary embodiment of the breast cancer pathological image diagnosis support system according to the present invention.

FIG. 7 is a block diagram showing a second exemplary embodiment of the breast cancer pathological image diagnosis support system according to the present invention. The system of this exemplary embodiment is different from the system according to the first exemplary embodiment shown in FIG. 1 in that the staining positive cell content rate calculating unit 125 also calculates staining intensity in addition to the staining positive cell content rate, and other configuration and operation are similar to those of the first exemplary embodiment.

In FIG. 7, a staining positive cell content rate and staining intensity calculating unit 725 reads the IHC image data and the tumor area from the IHC image data storage unit 134 and the IHC image tumor area information storage unit 136, respectively. Then, the staining positive cell content rate and staining intensity calculating unit 725 counts the number of staining positive cell nuclei and the number of staining negative cell nuclei in the tumor area to calculate the staining positive cell content rate, and further, calculates the staining intensity to output from the output device 112.

Figure 8:
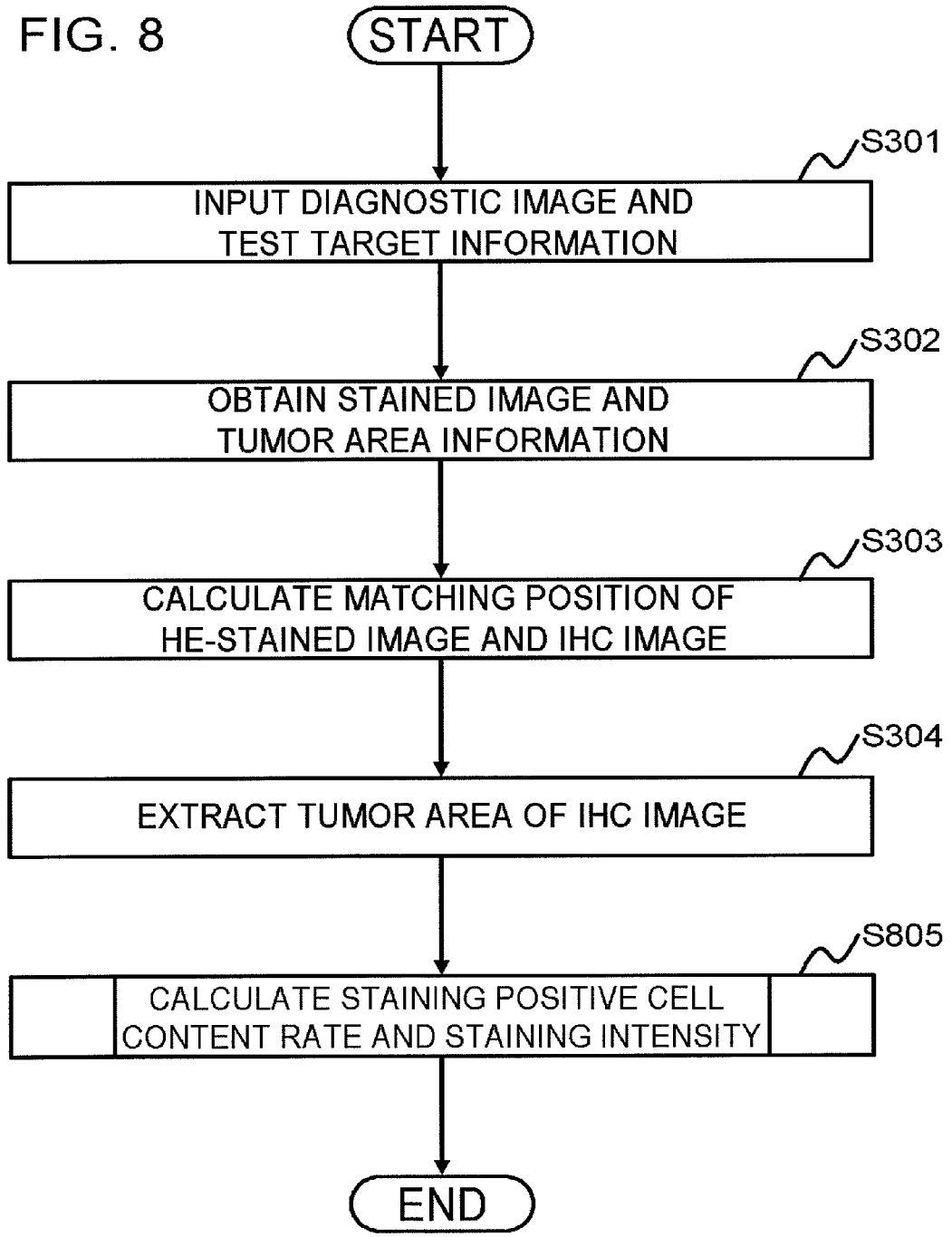
FIG. 8 is a flowchart for illustrating an example of the operation of the system shown in FIG. 7.

An example of operation of the system shown in FIG. 7 will be described below as the second exemplary embodiment of the breast cancer pathological image diagnosis support method and the breast cancer pathological image diagnosis support program according to the present invention with reference to flowcharts in FIGS. 8 to 10.

The process of this exemplary embodiment differs from that of the first exemplary embodiment shown in FIG. 3 in that this calculates not only the staining positive cell content rate but also the staining intensity, and other operation is similar to that of the first exemplary embodiment.

Figure 9:
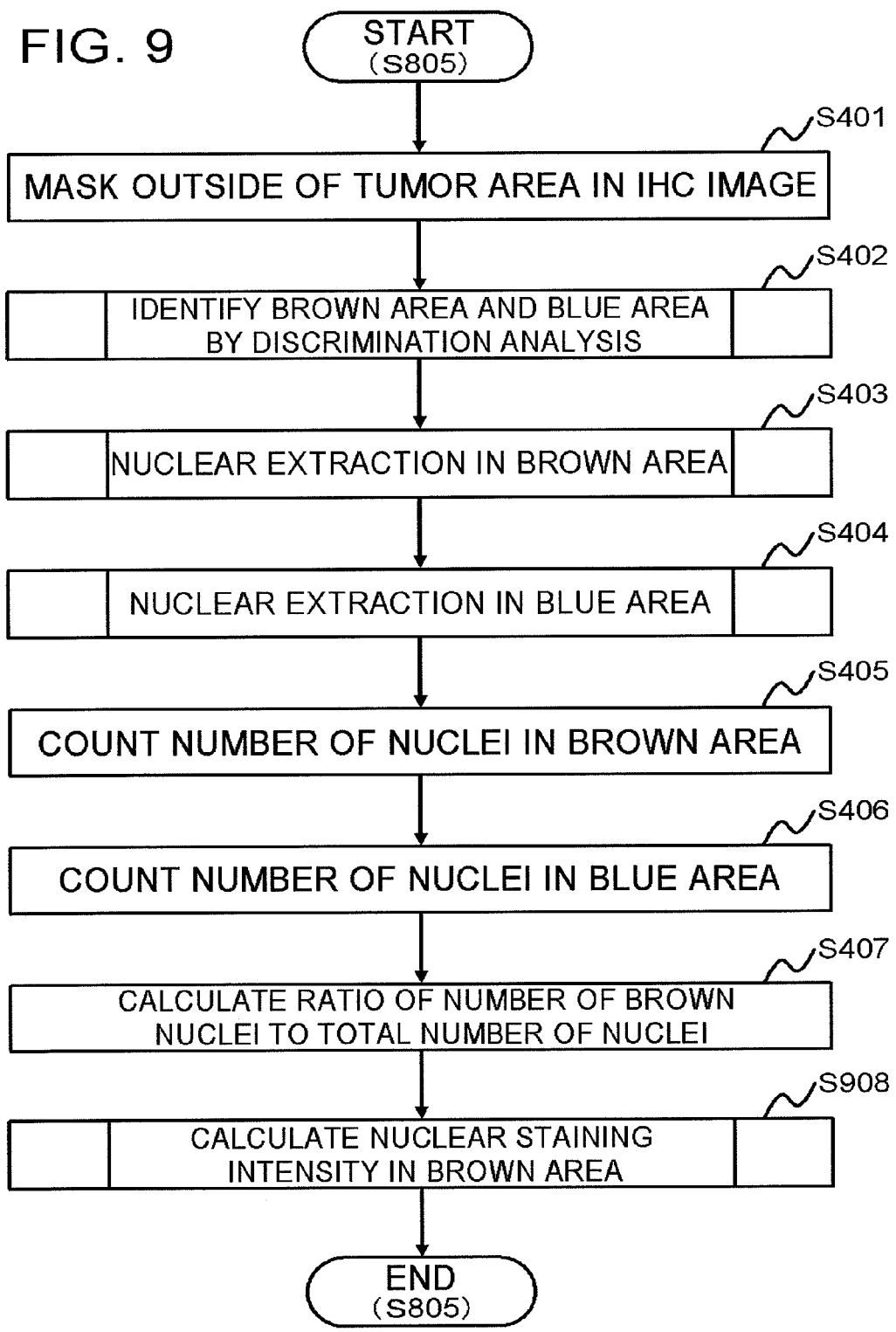
FIG. 9 is a flowchart for illustrating an example of the operation of the system shown in FIG. 7.
Figure 10:
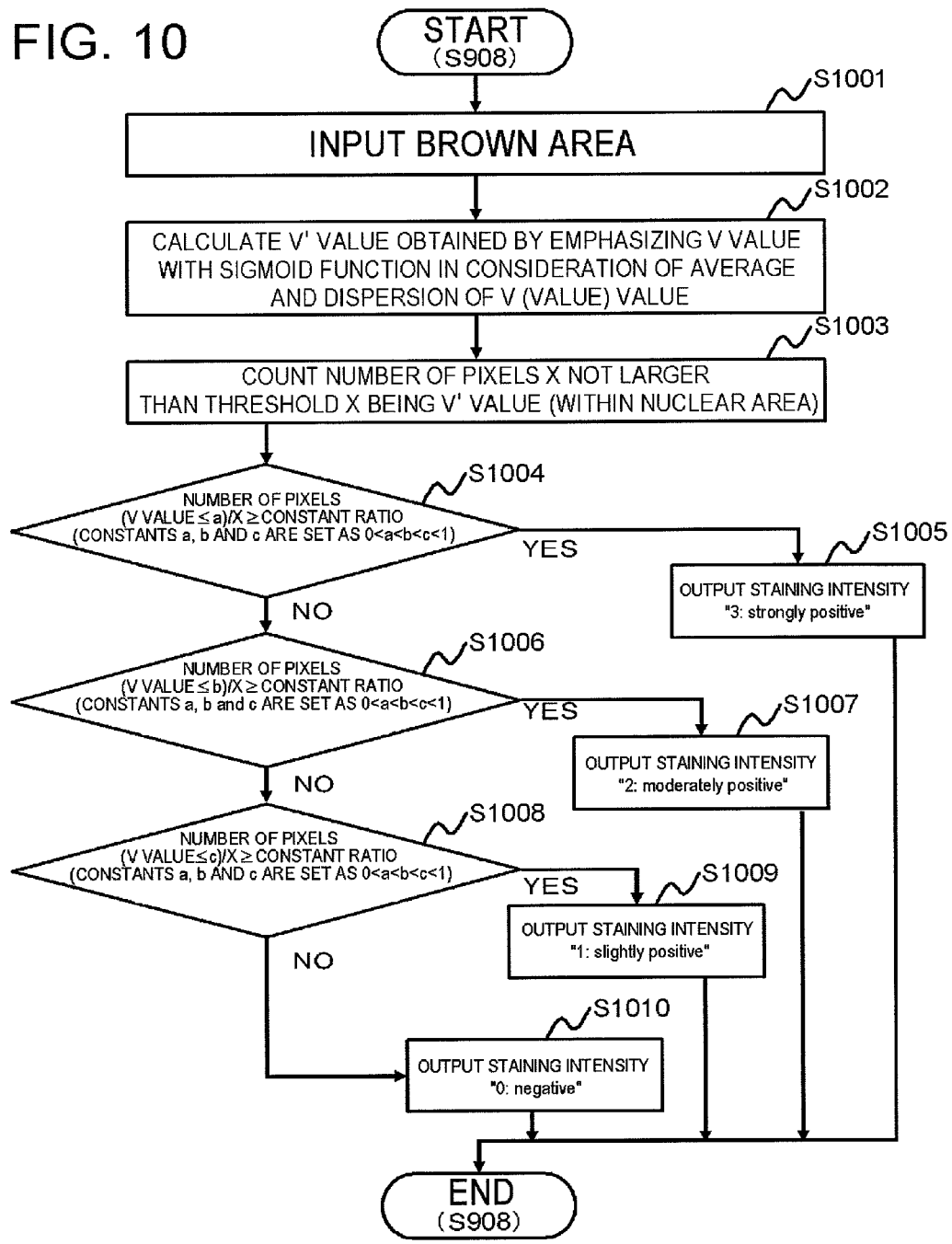
FIG. 10 is a flowchart for illustrating an example of the operation of the system shown in FIG. 7.

The staining positive cell content rate and staining intensity calculating unit 725 receives the IHC image data stored in the IHC image data storage unit 134 and the tumor area stored in the IHC image tumor area information storage unit 136, counts the number of staining positive cell nuclei and the number of staining negative cell nuclei in the tumor area to calculate the staining positive cell content rate, and calculates the staining intensity (0: negative, 1: slightly positive, 2: moderately positive, 3: strongly positive) to output from the output device 112 (step S805) The process is performed according to the procedures shown in FIGS. 9 and 10.

Figure 4:
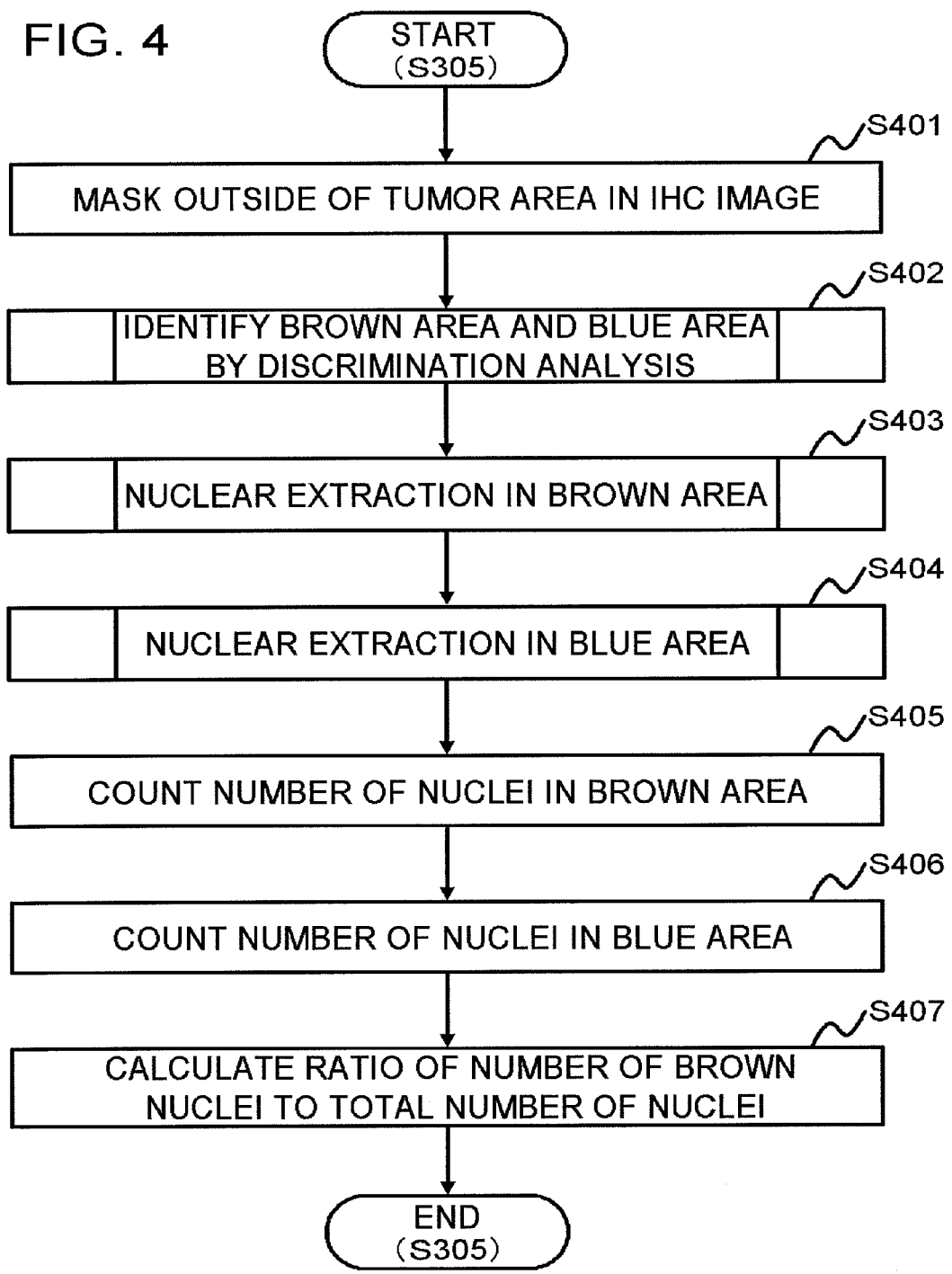
FIG. 4 is a flowchart for illustrating an example of the operation of the system shown in FIG. 1.
Figure 5:
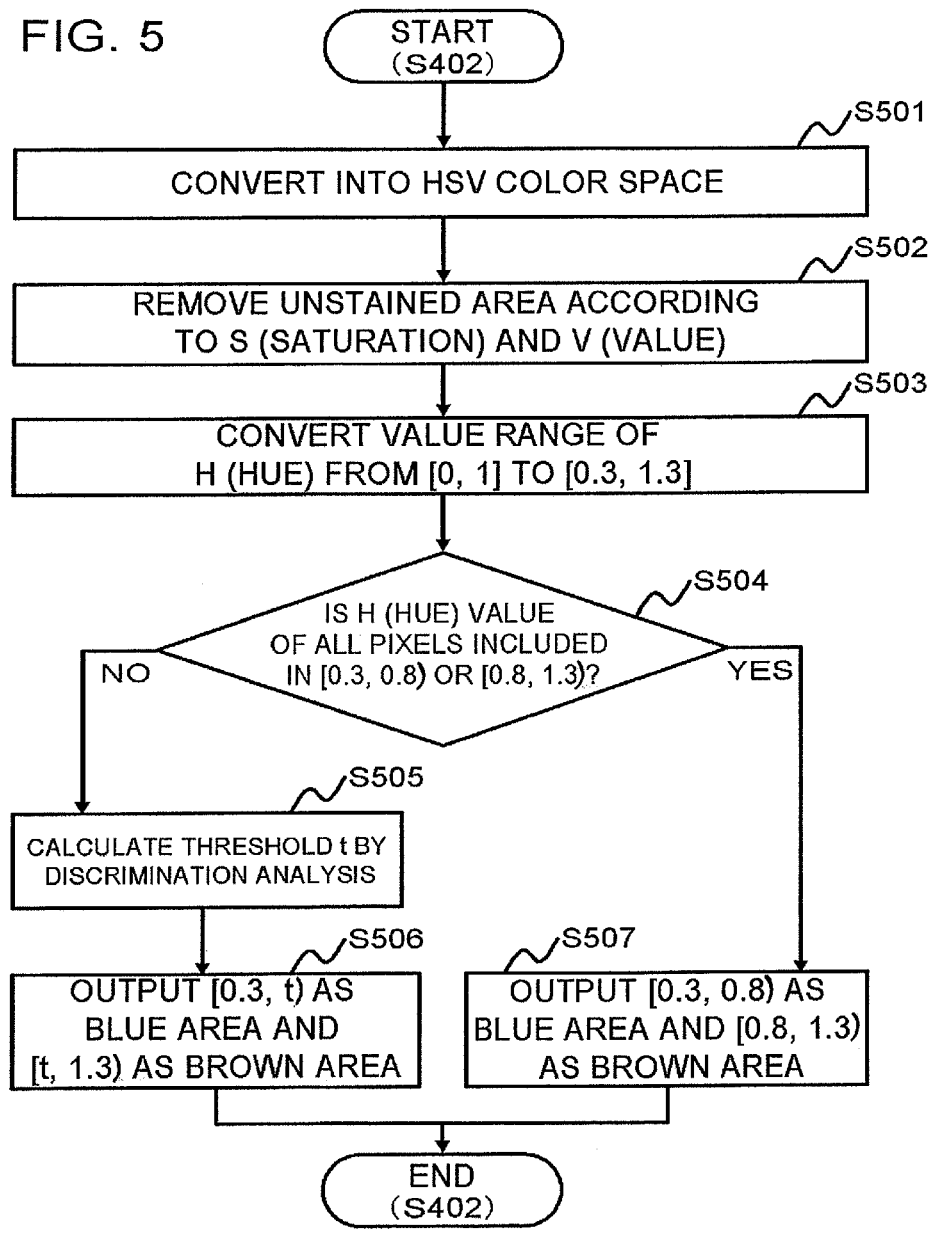
FIG. 5 is a flowchart for illustrating an example of the operation of the system shown in FIG. 1.
Figure 6:
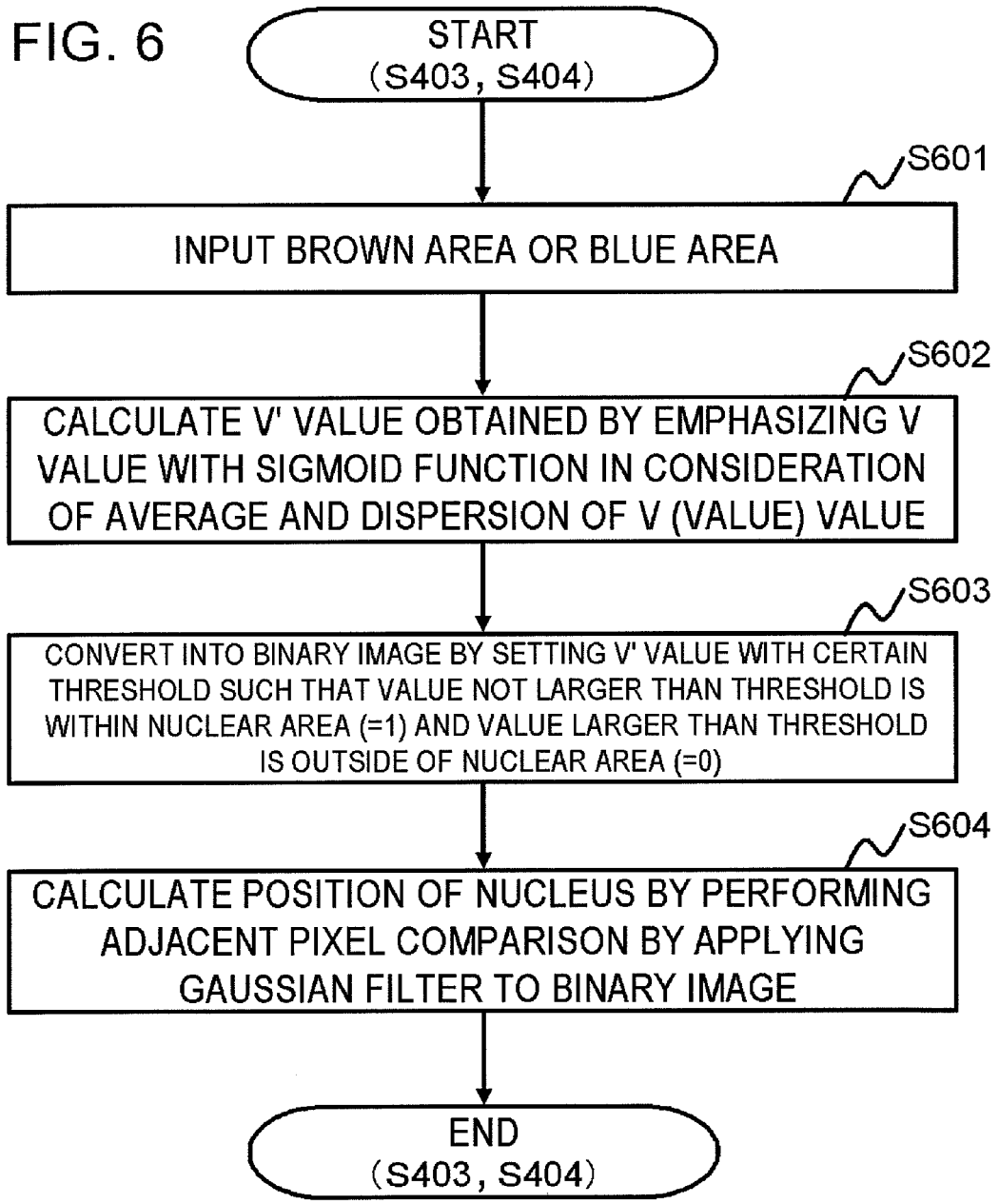
FIG. 6 is a flowchart for illustrating an example of the operation of the system shown in FIG. 1.

The process is the same as that of the first exemplary embodiment shown in FIG. 4 until the step S407 in FIG. 9. Next to the step S407, nuclear staining intensity is calculated in the brown area (step S908).

First, when the brown area determined at the step S402 in FIG. 9 is input (step S1001), the V' value obtained by emphasizing the V value with the sigmoid function is calculated in consideration of the average and the dispersion of the V (value) value (step S1002), and the number of pixels X, which is not larger than a threshold x being the V' value (within the nuclear area) is counted (step S1003).

Next, constants a, b and c are set as $0<a<b<c<1$, and when a ratio of the number of pixels satisfying a condition of V value $\leq a$ to the number of pixels in the nuclear area is not smaller than a certain ratio (step S1004), it is output as the staining intensity "3: strongly positive" (step S1005). If it is not the case, and when the ratio of the number of pixels satisfying a condition of V value $\leq b$ to the number of pixels in the nuclear area is not smaller than a certain ratio (step S1006), it is output as the staining intensity "2: moderately positive" (step S1007). If it is not the case, and when the ratio of the number of pixels satisfying a condition of V value $\leq c$ to the number of pixels in the nuclear area is not smaller than a certain ratio (step S1008), it is output as the staining intensity "1: slightly positive" (step S1009). If it is not the case, it is output as the staining intensity "0: negative" (step S1010).

An effect of this exemplary embodiment will be described below. Although only the staining positive cell content rate is presented to the doctor in the first exemplary embodiment, it is possible to present not only the staining positive cell content rate but also the staining intensity to the doctor or the like in this exemplary embodiment, and it is possible to provide the information more helpful to the diagnosis by the doctor, thereby supporting the diagnosis. Another effect of this exemplary embodiment is similar to that of the first exemplary embodiment.

Third Exemplary Embodiment

Figure 11:
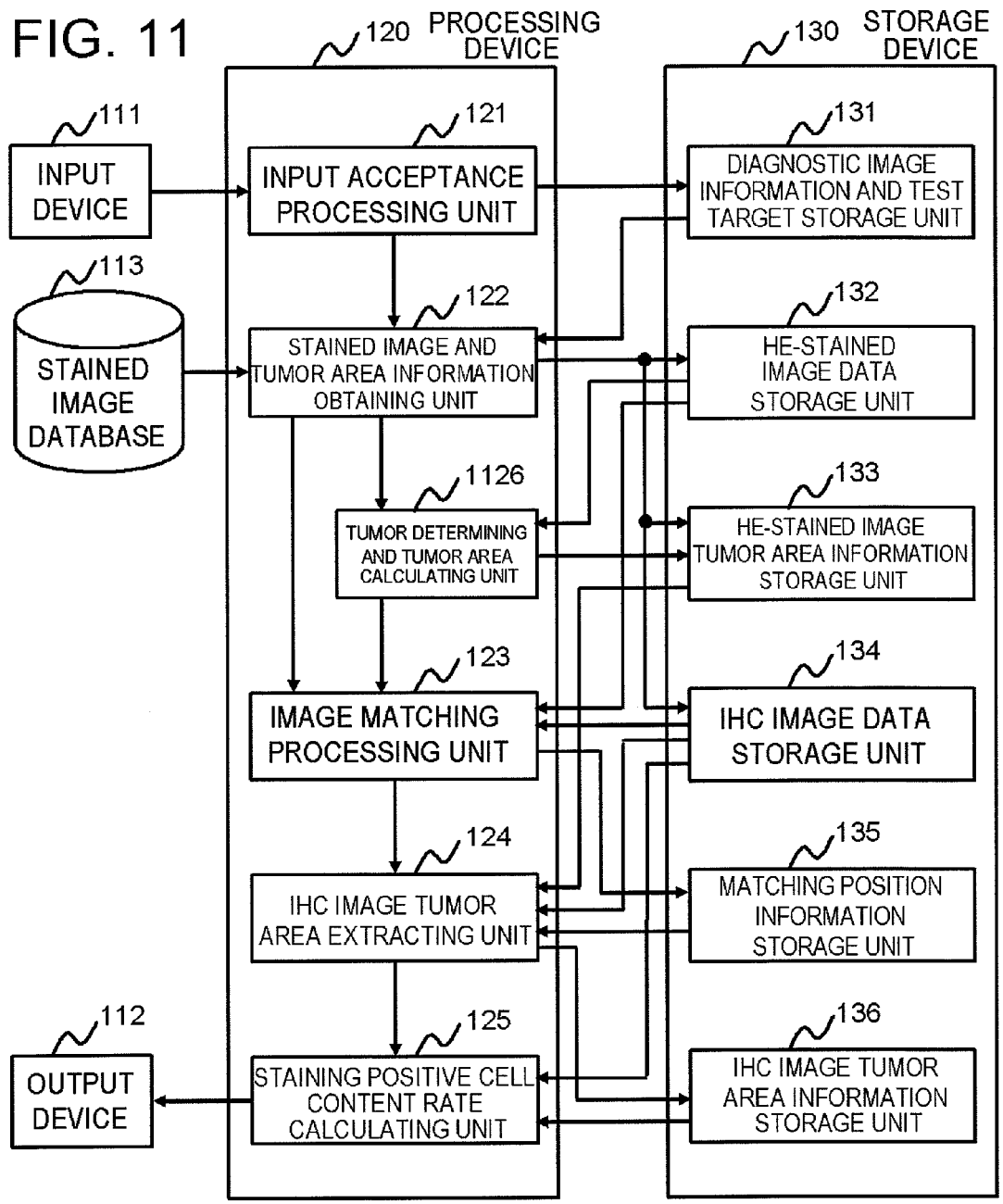
FIG. 11 is a block diagram showing a third exemplary embodiment of the breast cancer pathological image diagnosis support system according to the present invention.

FIG. 11 is a block diagram showing a third exemplary embodiment of the breast cancer pathological image diagnosis support system according to the present invention. The system of this exemplary embodiment differs from the system according to the first exemplary embodiment shown in FIG. 1 in that the system of this exemplary embodiment is provided with a tumor determining and tumor area calculating unit 1126 (tumor area calculating unit), and other configuration and operation are similar to those of the first exemplary embodiment. In addition, one or more HE-stained image, the IHC image, which is the specimen of the serial section adjacent to the specimen of the HE-stained image, and the specimen adjacent information of the above-described HE-stained image and the above-described IHC image are accumulated in the stained image database 113. In this exemplary embodiment, presence of the tumor area information calculated from the above-described HE-stained image or determined by the doctor or the like is not imperative.

In FIG. 11, the stained image and tumor area information obtaining unit 122 obtains the HE-stained image, the IHC image and the HE-stained image tumor area information 206 from the stained image database 113, and stores them in the HE-stained image data storage unit 132, the IHC image data storage unit 134 and the HE-stained image tumor area information storage unit 133 of the storage device 130, respectively. Herein, when the tumor area information 206 is present, the process shifts to the image matching processing unit 123; however, when the tumor area information 206 is not present, the process shifts to the tumor determining and tumor area calculating unit 1126.

The tumor determining and tumor area calculating unit 1126 reads the HE-stained image data from the HE-stained image data storage unit 132, determines the tumor and calculates the tumor area, and shifts the process to the image matching processing unit 123. As a method of the tumor determination and the tumor area calculation, a method disclosed in the patent document 1 may be utilized, for example.

An effect of this exemplary embodiment will be described below. In this exemplary embodiment, even when the tumor is not determined in the HE-stained image, a series of processes may be performed by providing the tumor determining and tumor area calculating unit, and it is possible to provide the information helpful to the diagnosis by the doctor, thereby supporting the diagnosis by presenting diagnostic information integrating from a cancer diagnosis to an immunohistochemically-stained image diagnosis to the doctors or the like. Another effect of this exemplary embodiment is similar to that of the first exemplary embodiment.

Meanwhile, in this exemplary embodiment, it is possible to calculate the staining intensity together with the staining positive cell content rate as in the case of the second exemplary embodiment.

Fourth Exemplary Embodiment

Figure 12:
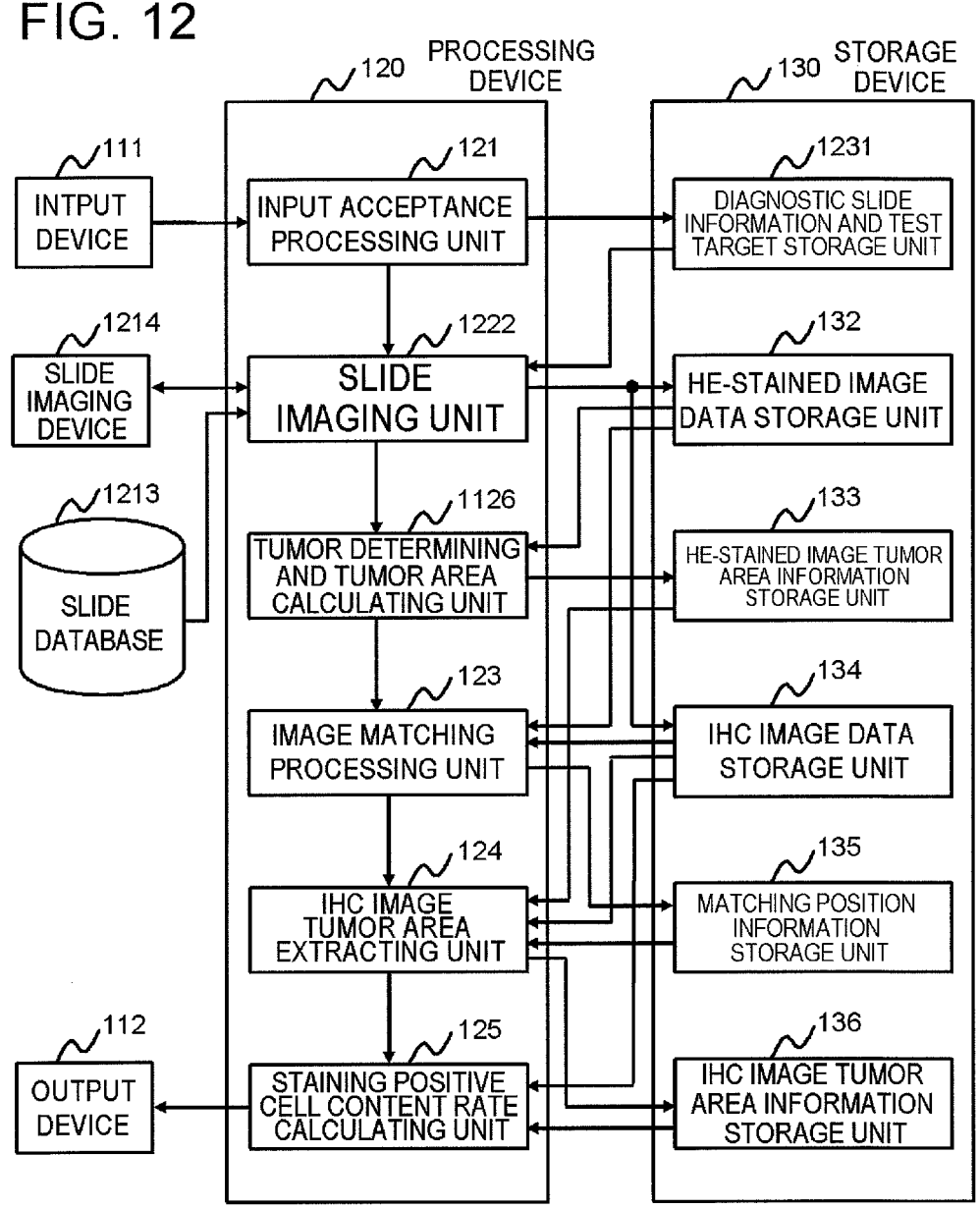
FIG. 12 is a block diagram showing a fourth exemplary embodiment of the breast cancer pathological image diagnosis support system according to the present invention.

FIG. 12 is a block diagram showing a fourth exemplary embodiment of the breast cancer pathological image diagnosis support system according to the present invention. The system of this exemplary embodiment includes a slide imaging unit 1222 (slide obtaining unit) which is provided in place of the stained image and tumor area information obtaining unit 122 (refer to FIG. 1 or the like), a slide database 1213 which is provided in place of the stained image database 113, and a diagnosis slide information and test target storage unit 1231 which is provided in place of the diagnostic image information and test target storage unit 131. Further, the system is provided with a slide imaging device 1214 and a tumor determining and tumor area calculating unit 1126. Other configuration and operation are similar to those of the first exemplary embodiment.

One or more HE-stained slide, an IHC slide, which is the specimen of the serial section adjacent to the specimen of the HE-stained slide, and the specimen adjacent information of the above-described HE-stained slide and the above-described IHC slide are accumulated in the slide database 1213. The relevant information regarding the subject is associated to each slide by the subject identifier. The slide imaging device 1214 images a specified slide to convert into digital data.

The input acceptance processing unit 121 accepts specification information of the slide to be diagnosed (slide identifier), and the specification information of the test type from the user and the like through the input device 111, stores them in the diagnostic slide information and test target storage unit 1231 of the storage device 130, and the process is shifted to the slide imaging unit 1222.

The slide imaging unit 1222 obtains the HE-stained slide and the IHC stained slide, which are the adjacent specimens to be diagnosed, from the slide database 1213. Further, the slide imaging unit 1222 obtains the HE-stained image and the IHC image by imaging the obtained slides by the slide imaging device 1214 to convert into the digital data. Then, these images are stored in the HE-stained image data storage unit 132 and the IHC image data storage unit 134 of the storage device 130, respectively, and the process is shifted to the tumor determining and tumor area calculating unit 1126. In this manner, the slide imaging unit 1222 combines the functions of the slide obtaining unit and the image obtaining unit in this exemplary embodiment.

An effect of this exemplary embodiment will be described below. In this exemplary embodiment, even when a pathological slide is not converted into digital data, a series of processes are performed by providing the slide imaging device, the slide database, and the slide imaging unit, and it is possible to provide the information helpful to the diagnosis by the doctor, thereby supporting the diagnosis, by presenting the diagnosis information integrating from the slide imaging, the cancer diagnosis to the immunohistochemically-stained image diagnosis to the doctor or the like. Another effect of this exemplary embodiment is similar to that of the first exemplary embodiment.

Meanwhile, it is possible to calculate the staining intensity together with the staining positive cell content rate in this exemplary embodiment, as in the case of the second exemplary embodiment.

The present invention is not limited to the above-described exemplary embodiments, and various modifications may be made. For example, an example in which the input acceptance processing unit 121 accepts the image identifier, which specifies the diagnostic image, is described in the above-described exemplary embodiment. However, the input acceptance processing unit 121 may accept not the image identifier but the subject identifier of the diagnostic target. In this case, the stained image and tumor area information obtaining unit 122 may search the stained image database 113 for the image having the subject identifier and the tumor area information.

The above-described processing device 120 may be composed of the computer formed of hardware resources (not shown) such as the CPU, the main memory, various calculating devices and an input/output interface. In this case, the CPU executes an application program read from the storage device 130 by using the main memory and the various calculating devices. All of or a part of functional blocks composing the processing device 120 may be realized by the application program (or a program code) recorded in the storage device 130, which is a recording medium.

Although the invention of the present application is described with reference to the exemplary embodiments as above, the invention of the present application is not limited to the above-described exemplary embodiments. Various modifications, which may be understood by one skilled in the art, may be made in the configuration and detail of the invention of the present application within the scope of the invention of the present application.

Also, this application is based upon and claims the benefit of priority from Japanese Patent Application No. 2007-51715 filed on Mar. 1, 2007, the disclosure of which is incorporated herein in its entirety by reference.

The invention claimed is:

1. A breast cancer pathological image diagnosis support device for supporting a diagnosis based on pathological images by using an HE-stained image and an IHC image as said pathological images of breast cancer, the device comprising:
   a computer processor; and
   a memory which stores a program implementing:
   a matching unit executed by the computer processor, which calculates a matching position of said HE-stained image and said IHC image;
   a specifying unit executed by the computer processor, which specifies, based on information of a tumor area specified in said HE-stained image and information of said matching position calculated by said matching unit, an area in the IHC image corresponding to the tumor area specified in the HE-stained image and specifies the specified area as a tumor area in the IHC image; and
   a calculating unit executed by the computer processor, which calculates a staining positive cell content rate in said tumor area based on information of the tumor area in said IHC image specified by said specifying unit,
   wherein said calculating unit converts image data of said tumor area of said IHC image into an HSV color space, calculates a threshold value by discrimination analysis of a value of H (hue) in the HSV color space of the image data, discriminates a brown area and a blue area in the tumor area of the IHC image on the basis of the calculated threshold value, extracts, in the tumor area of the IHC image, nucleus in the brown area to count the number of nuclei to obtain the number of staining positive cell nuclei, and extracts nucleus in the blue area to count the number of nuclei to obtain the number of staining negative cell nuclei, and calculates the staining positive cell content rate in said tumor area of the IHC image.

2. The breast cancer pathological image diagnosis support device as set forth in claim 1, wherein
   said matching unit binarizes a color scale of each pathological image of said HE-stained image and said IHC image, and calculates a position of the nucleus of said HE-stained image and said IHC image as the matching position, and
   said specifying unit matches the positions of the nucleus of said HE-stained image and said IHC image based on said matching position, and specifies the tumor area in said IHC image.

3. The breast cancer pathological image diagnosis support device as set forth in claim 1, wherein
   said matching unit calculates said matching position by phase-only correlation method.

4. The breast cancer pathological image diagnosis support device as set forth in claim 1, further comprising:
an information obtaining unit which obtains information of said tumor area in said HE-stained image.

5. The breast cancer pathological image diagnosis support device as set forth in claim 1, further comprising:
an image obtaining unit which obtains said HE-stained image and said IHC image as the pathological images to be diagnosed.

6. The breast cancer pathological image diagnosis support device as set forth in claim 1, further comprising:
an input accepting unit which accepts input of specification information of said pathological image to be diagnosed and specification information of a test type; and
a stained image database which stores said HE-stained image and said IHC image, wherein
said image obtaining unit obtains said HE-stained image and said IHC image from said stained image database based on said specification information.

7. The breast cancer pathological image diagnosis support device as set forth in claim 6, wherein
said specification information of said pathological image is an image identifier of said HE-stained image, and
said image obtaining unit obtains said HE-stained image having said image identifier and said IHC image adjacent to said HE-stained image from said stained image database.

8. The breast cancer pathological image diagnosis support device as set forth in claim 6, wherein
said specification information of said pathological image is an image identifier of said IHC image, and
said image obtaining unit obtains said IHC image having said image identifier and said HE-stained image adjacent to said IHC image from said stained image database.

9. The breast cancer pathological image diagnosis support device as set forth in claim 6, wherein
said specification information of said pathological image is a subject identifier of a diagnosis target, and
said image obtaining unit obtains said HE-stained image and said IHC image respective having said target identifier from said stained image database.

10. The breast cancer pathological image diagnosis support device as set forth in claim 6, wherein
said stained image database also stores said information of said tumor area in said HE-stained image, and
said information obtaining unit obtains said information of said tumor area in said HE-stained image from said stained image database.

11. The breast cancer pathological image diagnosis support device as set forth in claim 1, further comprising:
a tumor area calculating unit which calculates the tumor area in said HE-stained image obtained by said image obtaining unit, wherein
said information obtaining unit obtains said information of said tumor area in said HE-stained image calculated by said tumor area calculating unit.

12. The breast cancer pathological image diagnosis support device as set forth in claim 1, comprising:
an input accepting unit which accepts input of a slide identifier of a slide to be diagnosed and specification information of a test type;
a slide database which stores said slide; and
a slide obtaining unit which obtains said slide having said slide identifier from said slide database, wherein
said image obtaining unit obtains said HE-stained image and said IHC image by imaging said slide obtained by said slide obtaining unit.

13. The breast cancer pathological image diagnosis support device as set forth in claim 1, wherein
said calculating unit also calculates staining intensity in addition to said staining positive cell content rate, said staining intensity being indicated with several levels of positive or negative cell content rate within said tumor area, said levels respectively corresponding to several segments into which the V (value) value in said brown area of said IHC image from 0 to 1 is divided, and
said calculating unit calculates a V' value obtained by emphasizing the V(value) value with the sigmoid function in consideration of the average and the dispersion of the V (value) value, counts the number of pixels, which is not larger than a threshold being the V' value within the nuclear area, judges whether a ratio of the number of pixels of said nuclear area is not smaller than a certain ration or not, with respect to the number of pixels in each of said segments in the order of the V value of said segments from smaller or larger, and outputs the corresponding level as said staining intensity when said ratio of the number of pixels in the segment is not smaller than said certain ratio.

14. The breast cancer pathological image diagnosis support device as set forth in claim 2,
wherein said matching unit converts, into a binary image, each of pathological images of said HE-stained image and said IHC image, within respective said brown area and said blue area, on the basis of V (value), and calculates the positions of the nucleus of the binarized HE-stained image and said IHC image as the matching position, and
said calculating unit matches the positions of the nucleus of the binarized HE-stained image and said IHC image on said matching position, and specifies the tumor area in said IHC image.

15. The breast cancer pathological image diagnosis support device as set forth in claim 1,
wherein said matching unit converts, into a binary image, each of pathological images of said HE-stained image and said IHC image, within respective said brown area and said blue area, on the basis of V (value), and calculates the positions of the nucleus of the binarized HE-stained image and said IHC image as the matching position, and
said calculating unit matches the positions of the nucleus of the binarized HE-stained image and said IHC image on said matching position, and counts the number of nuclei in said brown area of said IHC image as the number of staining positive cell nuclei, counts the number of nuclei in said blue area of said IHC image as the number of staining negative cell nuclei, and calculates a staining positive cell content rate in the tumor area of said IHC image.

16. A method of supporting a diagnosis based on pathological images by using an HE-stained image and an IHC image as said pathological images of breast cancer, comprising:
matching, by a processing device, images to calculate a matching position of said HE-stained image and said IHC image;
specifying, by said processing device, based on information of a tumor area specified in said HE-stained image obtained at said information obtaining and information of said matching position calculated at said matching, an area in the IHC image corresponding to the tumor area specified in the HE-stained image, and specifying the specified area as a tumor area in the IHC image; and calculating a staining positive cell content rate in said tumor area based on information of the tumor area in said IHC image specified by said specifying step, wherein the calculating comprises converting image data of said tumor area of said IHC image into an HSV color space, calculating a threshold value by discrimination analysis of a value of H (hue) in the HSV color space of the image data, discriminating a brown area and a blue area in the tumor area of the IHC image on the basis of the calculated threshold value, extracting, in the tumor area of the IHC image, nucleus in the brown area to count the number of nuclei to obtain the number of staining positive cell nuclei, and extracting nucleus in the blue area to count the number of nuclei to obtain the number of staining negative cell nuclei, and calculating the staining positive cell content rate in said tumor area of the IHC image.

17. The breast cancer pathological image diagnosis support method as set forth in claim 16, wherein said matching by said processing device, binarizes a color scale of each pathological image of said HE-stained image and said IHC image and calculates a position of the nucleus of said HE-stained image and said IHC image as the matching position, and said specifying by said processing device, matches the positions of the nucleus of said HE-stained image and said IHC image based on said matching position, and specifies the tumor area in said IHC image.

18. The breast cancer pathological image diagnosis support method as set forth in claim 17, wherein said matching by said processing device, is calculating said matching position by phase-only correlation method.

19. The breast cancer pathological image diagnosis support method as set forth in claim 16, further comprising:

obtaining, by said processing device, the information of said tumor area in said HE-stained image.

20. The breast cancer pathological image diagnosis support method as set forth in claim 16, further comprising:

obtaining, by said processing device, said HE-stained image and said IHC image as the pathological images to be diagnosed.

21. The breast cancer pathological image diagnosis support method as set forth in claim 17, wherein said matching converts, into a binary image, each of pathological images of said HE-stained image and said IHC image, within respective said brown area and said blue area, on the basis of V (value), and calculates the positions of the nucleus of the binarized HE-stained image and said IHC image as the matching position, and said specifying matches the positions of the nucleus of the binarized HE-stained image and said IHC image on said matching position, and specifies the tumor area in said IHC image.

22. The breast cancer pathological image diagnosis support method as set forth in claim 16, wherein said matching converts, into a binary image, each of pathological images of said HE-stained image and said IHC image, within respective said brown area and said blue area, on the basis of V (value), and calculates the positions of the nucleus of the binarized HE-stained image and said IHC image as the matching position, and said specifying matches the positions of the nucleus of the binarized HE-stained image and said IHC image on said matching position, and counts the number of nuclei in said brown area of said IHC image as the number of staining positive cell nuclei, counts the number of nuclei in said blue area of said IHC image as the number of staining negative cell nuclei, and calculates a staining positive cell content rate in the tumor area of said IHC image.

23. A non-transitory computer-readable recording medium recording a program for supporting a diagnosis based on pathological images by using an HE-stained image and an IHC image as said pathological images of breast cancer, causing a computer to execute:

a matching procedure of calculating a matching position of said HE-stained image and said IHC image;

a specifying procedure of specifying, based on information of a tumor area specified in said HE-stained image and information of said matching position calculated in said matching procedure, an area in the IHC image corresponding to the tumor area specified in the HE-stained image and specifying the specified area as a tumor area in the IHC image; and a calculating procedure of calculating a staining positive cell content rate in said tumor area based on information of the tumor area in said IHC image specified by said specifying procedure, wherein said calculating procedure converts image data of said tumor area of said IHC image into an HSV color space, calculates a threshold value by discrimination analysis of a value of H (hue) in the HSV color space of the image data, discriminates a brown area and a blue area in the tumor area of the IHC image on the basis of the calculated threshold value, extracts, in the tumor area of the IHC image, nucleus in the brown area to count the number of nuclei to obtain the number of staining positive cell nuclei, and extracts nucleus in the blue area to count the number of nuclei to obtain the number of staining negative cell nuclei, and calculates the staining positive cell content rate in said tumor area of the IHC image.

24. The non-transitory computer-readable recording medium as set forth in claim 23, wherein said matching procedure is a procedure of binarizing a color scale of each pathological image of said HE-stained image and said IHC image, and calculating a position of the nucleus of said HE-stained image and said IHC image as the matching position, and said specifying procedure is a procedure of matching the positions of the nucleus of said HE-stained image and said IHC image based on said matching position, and specifying the tumor area in said IHC image.

25. The non-transitory computer-readable recording medium as set forth in claim 24, wherein said matching procedure is a procedure of calculating said matching position by phase-only correlation method.

26. The non-transitory computer-readable recording medium as set forth in claim 23, causing the computer to further execute:

an information obtaining procedure of obtaining the information of said tumor area in said HE-stained image.

27. The non-transitory computer-readable recording medium as set forth in claim 23, causing the computer to further execute:

an image obtaining procedure of obtaining said HE-stained image and said IHC image as the pathological images to be diagnosed.

28. A breast cancer pathological image diagnosis support device for supporting a diagnosis based on pathological images by using an HE-stained image and an IHC image as said pathological images of breast cancer, the device comprising:

a computer processor; and a memory which stores a program implementing:

matching means executed by the computer processor, for calculating a matching position of said HE-stained image and said IHC image;

specifying means executed by the computer processor, for specifying, based on information of a tumor area specified in said HE-stained image and information of said matching position calculated by said matching means, an area in the IHC image corresponding to the tumor area specified in the HE-stained image and specifies the specified area as a tumor area in the IHC image; and calculating means executed by the computer processor, for calculating a staining positive cell content rate in said tumor area based on information of the tumor area in said IHC image specified by said specifying means, wherein said calculating means converts image data of said tumor area of said IHC image into an HSV color space, calculates a threshold value by discrimination analysis of a value of H (hue) in the HSV color space of the image data, discriminates a brown area and a blue area in the tumor area of the IHC image on the basis of the calculated threshold value, extracts, in the tumor area of the IHC image, nucleus in the brown area to count the number of nuclei to obtain the number of staining positive cell nuclei, and extracts nucleus in the blue area to count the number of nuclei to obtain the number of staining negative cell nuclei, and calculates the staining positive cell content rate in said tumor area of the IHC image.

* * * * *